United States Patent

Dexter et al.

[11] B 4,001,299
[45] Jan. 4, 1977

[54] HINDERED HYDROXYPHENYLALKANOATES OF SUBSTITUTED ISOPROPANOLS

[75] Inventors: Martin Dexter, Briarcliff Manor; David Herbert Steinberg, Bronx, both of N.Y.

[73] Assignee: Ciba-Geigy Corporation, Ardsley, N.Y.

[22] Filed: Dec. 12, 1974

[21] Appl. No.: 532,140

[44] Published under the second Trial Voluntary Protest Program on March 2, 1976 as document No. B 532,140.

[52] U.S. Cl. .............................. 260/473 S; 44/70; 252/407; 260/45.8 N; 260/45.85 R; 260/309.5; 260/473 F
[51] Int. Cl.² ................ C07C 149/20; C07C 69/76
[58] Field of Search ..................... 260/473 S, 473 F

[56] References Cited

FOREIGN PATENTS OR APPLICATIONS

| | | | |
|---|---|---|---|
| 288,839 | 1967 | Australia | 260/473 |
| 1,436,393 | 1966 | France | 260/473 |
| 2,133,374 | 1/1972 | Germany | 260/473 |

Primary Examiner—John F. Terapane
Attorney, Agent, or Firm—Luther A. R. Hall

[57] ABSTRACT

The compounds are esters having the formula

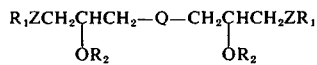

wherein $R_1$ is alkyl, cycloalkyl, alkylthioethyl or alkylpolyoxyalkylene, $R_2$ is the group

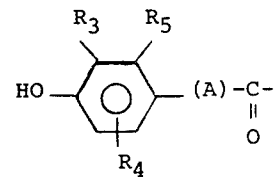

$R_3$ is hydrogen, alkyl, cycloalkyl or α-methylbenzyl, $R_4$ is alkyl or cycloalkyl, $R_5$ is hydrogen or alkyl, provided when $R_3$ is hydrogen, $R_5$ is alkyl and $R_4$ is located on the carbon atom ortho to the hydroxyl group, A is a covalent carbon bond or lower alkylene, Q is the group

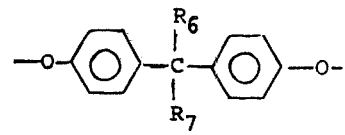

$R_6$ and $R_7$ are independently hydrogen or alkyl, and Z is oxygen or sulfur.

The esters of this invention are prepared by usual esterification procedures from a substituted isopropanol and an acid or a derivative thereof, preferably the methyl ester.

The substituted isopropanols are prepared by the reaction of bis-glycidyl ethers of polyhydric phenols or of 1,3-diglycidyl derivatives of hydantoin with a mercaptide or alkoxide.

The compounds are useful as stabilizers for organic materials, especially polyolefins, which degrade upon exposure to light and heat.

4 Claims, No Drawings

HINDERED HYDROXYPHENYLALKANOATES OF SUBSTITUTED ISOPROPANOLS

DETAILED DISCLOSURE

This invention pertains to substituted isopropanol esters of hindered hydroxyphenylalkanoic acids and to organic materials normally subject to oxidative, thermal and UV light degradation stabilized with said ester compounds.

More specifically the compounds of this invention are those having the formula

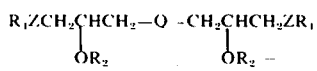

wherein
$R_1$ is alkyl of 1 to 30 carbon atoms, cycloalkyl of 5 to 12 carbon atoms, alkylthioethyl of 4 to 27 atoms in the chain or alkylpolyoxyalkylene of 4 to 27 atoms in the chain,
$R_2$ is the group

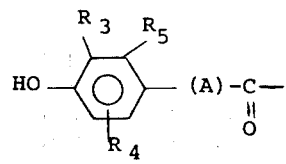

$R_3$ is hydrogen, alkyl of 1 to 8 carbon atoms, cycloalkyl of 5 to 6 carbon atoms or α-methylbenzyl,
$R_4$ is alkyl of 1 to 8 carbon atoms or cycloalkyl of 5 to 6 carbon atoms,
$R_5$ is hydrogen or lower alkyl of 1 to 4 carbon atoms, or $R_3$ and $R_5$ together are a butylene chain which, together with the phenyl ring, form a tetrahydronaphthyl group, and provided when $R_3$ is hydrogen, $R_5$ is alkyl and $R_4$ is located on the carbon atom ortho to the hydroxyl group,
A is a covalent carbon bond or a straight or branched lower alkylene having 1 to 8 carbon atoms,
Q is the group

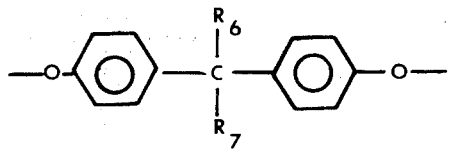

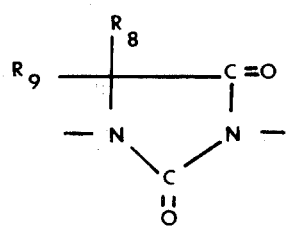

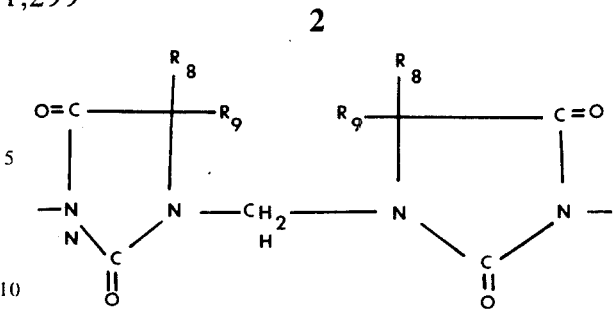

or

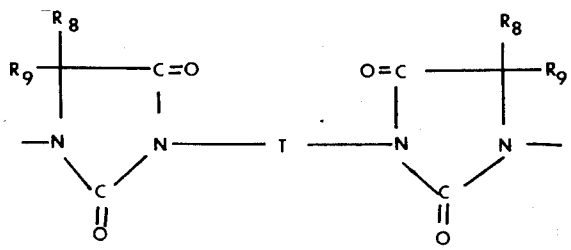

$R_6$ is hydrogen or alkyl of 1 to 4 carbon atoms,
$R_7$ is hydrogen or alkyl of 1 to 8 carbon atoms,
$R_8$ is hydrogen, alkyl of 1 to 8 carbon atoms or aryl of 6 or 10 carbon atoms,
$R_9$ is hydrogen or alkyl of 1 to 4 carbon atoms, or $R_8$ and $R_9$ together form a lower alkylene chain of 4 to 7 carbon atoms,
T is alkylene of 1 to 12 carbon atoms, and
Z is oxygen or sulfur.

The $R_1$ group can be alkyl of 1 to 30 carbon atoms such as methyl, n-butyl, n-octyl, t-dodecyl, n-octadecyl, n-tetracosanyl or n-triacontanyl. Preferably $R_1$ is alkyl of 1 to 18 carbon atoms, such as methyl, n-butyl, n-dodecyl or n-octadecyl. Most preferably for use in stabilizing polyolefins such as polypropylene, polyethylene and olefin copolymer $R_1$ is alkyl of 8 to 18 carbon atoms.

The $R_1$ group can be cycloalkyl of 5 to 12 carbon atoms such as cyclopentyl, cyclohexyl, cyclooctyl or cyclododecyl.

$R_1$ is also alkylthioethyl of 4 to 27 atoms in the chain such as 2-methylthioethyl, 2-(n-octylthio)ethyl and 2-tetracosanylthio)ethyl.

$R_1$ can also be alkylpolyoxyalkylene of 4 to 27 atoms in the chain having the general structure $R°(OC_nH_{2n})_h$ or $R°(OCH_2CHR')_h$ where $R°$ is alkyl of 1 to 18 carbon atoms, $n$ is 2 to 4, $R'$ is hydrogen, methyl or ethyl and $h$ is 1 to 3.

The $R_3$ and $R_4$ groups can be straight or branched lower alkyl groups, having 1 to 8 carbon atoms as for example, methyl, ethyl, isopropyl, n-butyl, tert-butyl, tert-amyl or n-octyl. $R_3$ and $R_4$ can also be cycloalkyl of 5 to 6 carbon atoms such as cyclopentyl or cyclohexyl. $R_3$ can also be α-methylbenzyl.

Preferably $R_3$ is a straight or branched alkyl group of 1 to 4 carbon atoms, such as methyl, ethyl, isopropyl or tert-butyl. Most preferably $R_3$ is methyl or tert-butyl.

Preferably $R_4$ is a branched alkyl of 3 to 8 carbon atoms, such as isopropyl, sec-butyl, tert-butyl, secamyl, tert-amyl, sec-octyl or tert-octyl. Most preferably R$_4$ is tert-butyl.

Preferably R$_5$ is hydrogen or alkyl of 1 to 3 carbon atoms, such as methyl, ethyl or n-propyl. Most preferably R$_5$ is hydrogen or methyl.

A is a covalent carbon bond or a straight or branched lower alkylene of 1 to 8 carbon atoms such as methylene, ethylene, 2,3-propylene, trimethylene, 1,1-dimethylethylene, 1,1-butylidene, 2-methyl-1,1-propylidene or 1,1-octylidene. Preferably A is a straight chain alkylene of 1 to 3 carbon atoms, that is, methylene, ethylene or trimethylene. Most preferably A is methylene or ethylene.

R$_6$ is hydrogen or alkyl of 1 to 4 carbon atoms such as methyl, ethyl or n-butyl. Preferably R$_6$ is hydrogen or methyl. Most preferably R$_6$ is methyl.

R$_7$ is hydrogen or alkyl of 1 to 8 carbon atoms such as methyl, ethyl, n-butyl or n-octyl. Preferably R$_7$ is hydrogen or alkyl of 1 to 3 carbon atoms such as methyl, ethyl or n-propyl. Most preferably R$_7$ is methyl.

R$_8$ is hydrogen, alkyl of 1 to 8 carbon atoms such as methyl, ethyl, n-propyl, isopropyl, sec-butyl, n-amyl or n-octyl. Preferably R$_8$ is hydrogen or alkyl of 1 to 4 carbon atoms such as methyl, ethyl, isopropyl or n-butyl. Most preferably R$_8$ is alkyl of 1 to 4 carbon atoms.

R$_8$ is also aryl of 6 or 10 carbon atoms such as phenyl or α-naphthyl.

R$_9$ is hydrogen or lower alkyl of 1 to 4 carbon atoms such as methyl, ethyl or n-butyl. Preferably R$_9$ is hydrogen or methyl. Most preferably R$_9$ is methyl.

R$_8$ and R$_9$ together form a lower alkylene chain of 4 to 7 carbon atoms and with the carbon atom to which both are attached form a cycloalkane attached to the hydantoin ring at a common spiro carbon. Preferably R$_8$ and R$_9$ together form a pentamethylene group.

T is alkylene of 1 to 12 carbon atoms such as methylene, ethylene, 1,4-butylene, hexamethylene or dodecamethylene.

The esters of this invention are prepared by usual esterification procedures from the appropriate substituted 2-propanol and an acid of the formula I

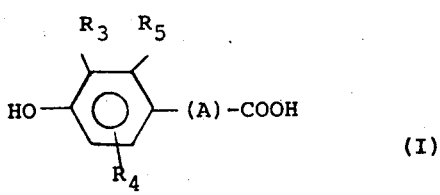

(I)

an acid halide or acid anhydride thereof or from the corresponding lower alkyl, preferably methyl, ester.

The acid halide derivatives of the above cited acids are made in a conventional manner using standard halogenating agents such as thionyl chloride, phosphorus trichloride and phosphorus oxychloride.

The lower alkyl esters, usually methyl, are conveniently made by an acid catalyzed reaction of the above-cited acid with a lower alcohol, such as methanol.

Where A is ethylene or substituted ethylene, the lower alkyl esters are conveniently made by reaction of a substituted phenol (II) with an acrylate ester as represented below.

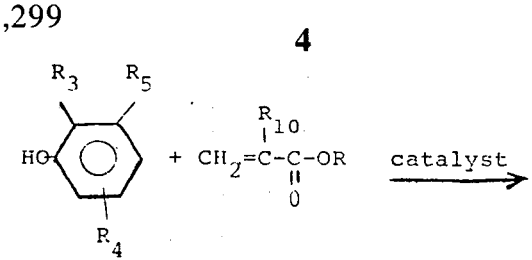

(II)

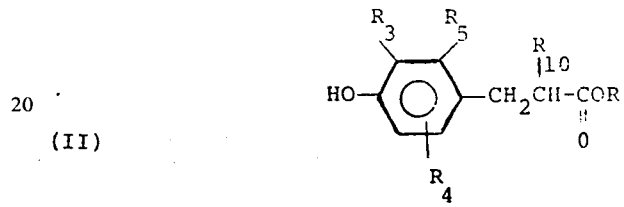

where R$_{10}$ is hydrogen or lower alkyl of 1 to 6 carbon atoms and R is alkyl of 1 to 4 carbon atoms. Processes of this type are disclosed for example in U.S. Pat. No. 3,247,240 (Apr. 9, 1966) and U.S. Pat. No. 3,364,250 (Jan. 16, 1968).

The above-described ester intermediates may also be made by reacting a substituted phenol with an acrylonitrile as represented below.

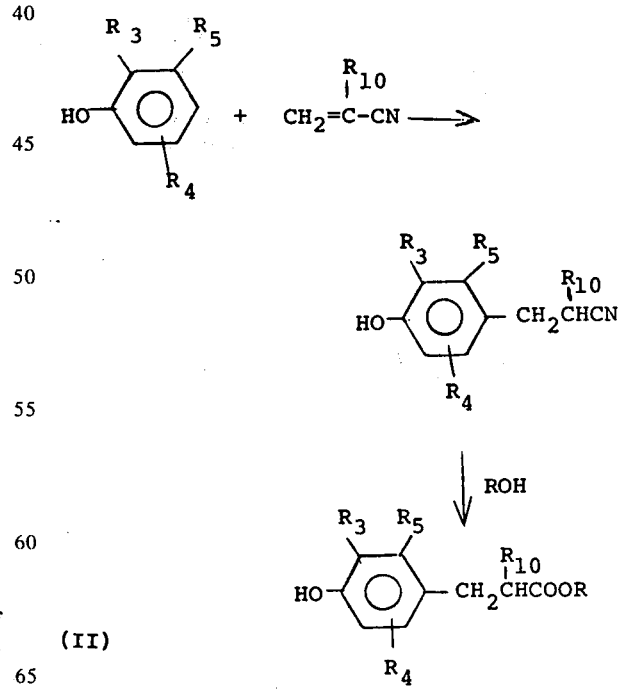

(II)

This reaction is analogous to that disclosed in U.S. Pat. No. 3,121,732 (Feb. 18, 1964).

The acids where A is methylene are conveniently made by the sequence below

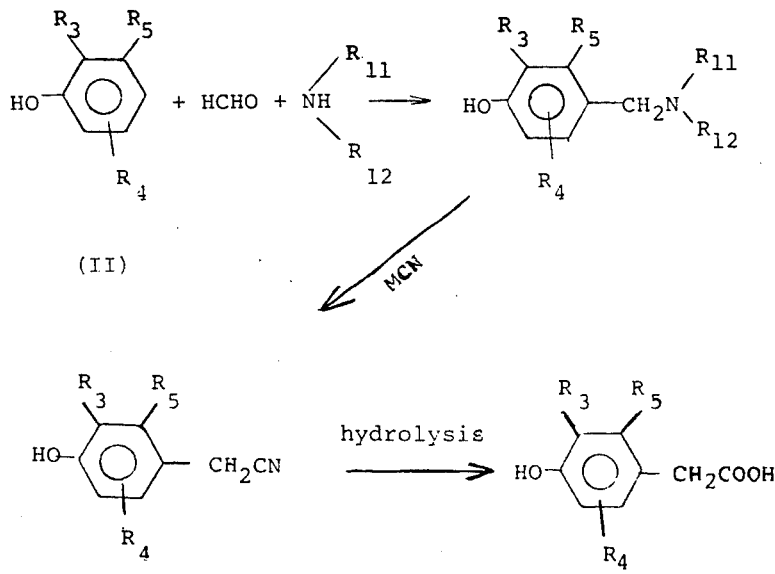

where M is an alkali metal such as sodium or potassium and $R_{11}$ and $R_{12}$ are lower alkyl of 1 to 8 carbon atoms or together form a morpholine or piperidine ring with the nitrogen atom. Preferably $R_{11}$ and $R_{12}$ are methyl.

Substitution of higher aldehydes such as n-butanal or n-octanal for formaldehyde in the reactions outlined in the previous paragraph leads to the preparation of acids of formula (I) where A is 1,1-alkylidene.

Acids of formula I can also be prepared by reaction of substituted phenolate anions with appropriate halogenoalkane carboxylate esters, amides or nitriles where A may be straight or branched alkylene of 2 to 8 carbon atoms.

Most of the di- and trialkylated phenols (II) contemplated for use as starting materials to make the compounds of this invention are known compounds which are available commercially. The preparation of 2,6-diisopropyl-3-methylphenol and 2,6-di-tert-butyl-3-methylphenol is disclosed in Japanese patent application 7015,491. The preparation of 2,3-dimethyl-6-tert-butylphenol is disclosed by G. Parc, *Revue de L'Institut Francais du Petrole*, XV, 693 (1960). Other substituted phenols may be made by the selected alkylation of phenolic starting materials using acid catalysis such as p-toluene sulfonic acid and selected olefins such as propylene, isobutylene and 2,4,4-trimethylpentene-1.

Although $R_4$ may be either ortho to the hydroxyl group or the A group, preferably $R_4$ is ortho to the hydroxyl in esters of this invention.

The substituted isopropanol intermediates are reacted with the hindered phenolalkanoic acid derivatives described previously to prepare the esters of this invention in the presence of a suitable basic catalyst such as sodium methoxide, lithium amide or lithium hydride.

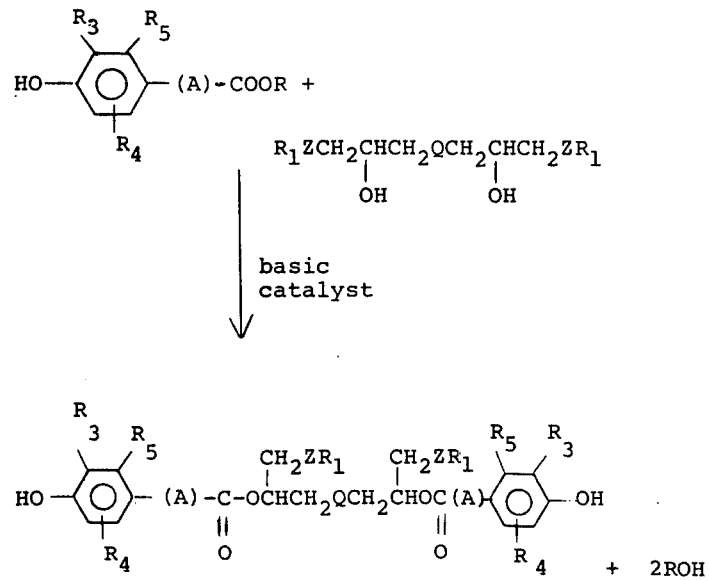

The key substituted isopropanol intermediates required to prepare the esters of this invention are conveniently made from glycidyl ethers of polyhydric phenols or from N-glycidyl derivatives of hydantoins.

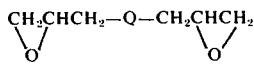

1. $R_1Z^-M^+$ (solvent optional)
2. $H^+X^-$

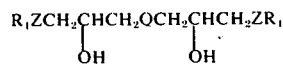

where $R_1$ and Z are defined as before, $M^+$ is a cation such as lithium, sodium or potassium and $X^-$ is an anion such as chloride or bromide.

These substituted 2-propanols are useful as chemical intermediates in the preparation of stabilizers of this invention and a myriad of other products such as synergists, extreme pressure additives for lubricants, pesticides, fuel additives and the like.

Esters of 3,5-dialkyl-4-hydroxyphenylalkanoic acids and alkane polyols are described in U.S. Pat. No. 3,644,482. Many of these compounds are crystalline or vitreous solids which are highly effective stabilizers against thermo-oxidative aging, ie they are solid antioxidants. Moreover they generally have only limited solubility in those solvents employed technically in large amounts such as aliphatic hydrocarbons.

These properties are highly advantageous in many applications, but represent disadvantages in others. It is thus difficult to utilize these solid compounds in technical processes in which the additives are pumped, proportioned and fed in fluid form, for example in hydrocarbon solution polymerization processes.

Somewhat related, sulfur-containing esters of 3,5-dialkyl-4-hydroxyphenylalkanoic acid are described in U.S. Pat. Nos. 3,285,855 and 3,441,575. These are the 2-alkylthioethyl esters, some being liquids and others solids.

Esters of 3,5-dialkyl-4-hydroxyphenylalkanoic acids and mixtures of at least two non-identical alkanediols are described in U.S. Pat. No. 3,779,945. These mixed esters do provide very suitable stabilization for organic materials subject to degradation, and in addition are liquids which can be pumped, proportioned and fed and which are quite soluble in organic solvents permitting their use in highly concentrated solutions.

The esters of this invention are also liquids which exhibit all the processing, solubility and utility advantages shown by the mixed esters described in U.S. Pat. No. 3,779,945.

The substrates of particular importance are olefin polymers such as polyethylene, polypropylene, olefin copolymers and blends thereof. Polypropylene is especially well stabilized with the compounds of this invention.

The stabilizers of this invention are particularly useful in protecting polymer compositions subjected to high temperature processing as well as end uses involving elevated temperatures.

The esters of this invention exhibit good stabilization activity in polypropylene. is the absence of a thio ester costabilizer such as distearyl $\beta$-thiodipropionate (DSTDP), but with the addition of DSTDP co-stabilizer, the stabilization protection afforded polypropylene increases greatly in some cases far exceeding that provided in similar formulations by commercial stabilizers described in U.S. Pat. No. 3,285,855 or by liquid mixed ester stabilizers described in U.S. Pat. No. 3,779,945.

The high degree or protection afforded polypropylene by the esters of this invention occurs at a low molar concentration of the active hindered phenol moiety compared to that of many commercial stabilizers. In addition, the less additive required in a polymer composition usually benefits retention of its basic physical properties.

It is understood that the scope of the invention is not limited by the following postulations nor that the stabilization effectiveness of the esters of this invention necessarily results from the proposed explanations thereof or or by the schematic representations presented. Although the reason for this particularly effective stabilization activity of the esters of this invention is unknown, it is theorized that the molecular structure of these esters must in some way permit a more efficacious utilization of the hindred phenol part of the molecules in the polypropylene system allowing less of the hindered phenol to perform the necessary stabilization function.

While the liquid physical nature of these esters may well facilitate their introduction and compatibilization in the amorphous areas of the polypropylene system where stabilization activity is most needed, it is postulated that the molecular structure of the esters is significantly different from the prior art stabilizers and that this difference in structure may well account for the great effectiveness of the esters of this invention.

These esters are all derived from substituted isopropanols having a long alkylthio or alkoxy solubilizing hydrocarbon substituent on the 3-carbon atoms and being coupled on the 1-carbon atoms with an oxyaryleneoxy or an N,N'-heterocyclic moiety. This forms a rather rigid internal molecular structure having good solubility properties having attached just on each end an active hindered phenol moiety and on the extreme outside of molecule in each direction a long solubilizing hydrocarbon moiety. This comination of molecular structure with concomitant solubility and physical properties affords good stabilization to polypropylene systems.

The prior art stabilizers are of four general types all differing significantly from the instant esters. In Type 1 a plurality of hindered phenol moieties surround a small hydrocarbon linking group. These materials are generally solids and relatively high melting materials with concomitant limited solubility in aliphatic hydrocarbon solvents. See U.S. Pat. No. 3,644,482.

In Type 2, the hindered phenol moiety is joined by a single long hydrocarbon chain sometimes containing a heteroatom such as sulfur. The 2-(n-alkylthio)ethyl esters related to the esters of this invention fall in this class. (See U.S. Pat. Nos. 3,330,859 and 3,441,575.)

In Type 3, two hindered phenol moieties are attached to an alkylene chain sometimes containing a heteroatom such as sulfur. (See U.S. Pat. No. 3,644,482).

In Type 4, mixed esters derived from a hindered phenolalkanoic acid and a mixture of alkyl substituted alkanediols result in liquid stabilizers having two hindered phenol moieties attached to an alkylene chain substituted with pendant lower alkyl groups (See U.S. Pat. No. 3,779,945).

A comparison of the test data on the best ester compounds of Types 1-4 described above and given in U.S. Pat. Nos. 3,285,855, 3,758,549 and 3,779,945 with test data on the esters of the present invention is given in Example 8, Table I. The esters of this invention at only 40% the concentration of the best prior art esters exhibit equal or better stabilization effectiveness in polypropylene.

Schematically these types of stabilizers may be represented below where + represents a hindered phenolic moiety, and — a short linking chain or pendant group and a long solubilizing hydrocarbon chain which may include a hereroatom such as oxygen or sulfur therein.

A comparison of these schematic models clearly indicates that the esters of the present invention are structurally and configurationally different and are not anticipated or suggested by the prior art compounds.

Type 1 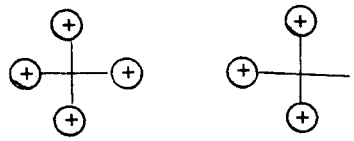

Type 2 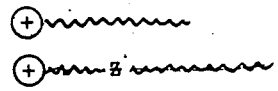

Type 3 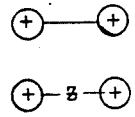

Type 4 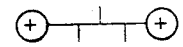

Esters of this invention

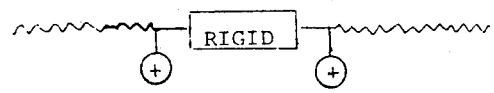

The ester compounds of the present invention provide excellent stabilization protection not only for polymeric substrates such as polyolefins, polyacetals, polyesters and polyamides, but also for non-polymeric substances such as oils which undergo thermal and actinic degradation.

For many purposes, it is convenient or even necessary that the stabilizer additive be a solid, preferably white, somewhat high melting material. This is especially true for polymeric substrates where small amounts of the additive are to be isolated then weighed accurately and added discretely into the polymeric system to be stabilized.

The compounds of the instant invention provide an equally beneficial physical form for such stabilizers are essentially colorless, high boiling liquids. These materials are stable, possess the requisite structures for enhancing solubility and compatibility in the substrates to be stabilized and provide by their totally liquid nature, as contrasted to a high-melting solid or a low-melting semi-solid, a particularly convenient method of addition to the substrate systems. The compounds of this invention can be accurately metered and monitored into the substrate systems to be stabilized using standard liquid pumping devices.

The esters of the invention are expected to find particular utility in stabilizing liquid substrates such as oils and in stabilizing polymeric substrates where liquid pumping devices can be expeditiously employed in adding the stabilizers during polymer processing.

The hindered hydroxyphenyl alkanoates of this invention are stabilizers of organic material normally subject to thermal and oxidative deterioration. Materials which are thus stabilized include synthetic organic polymeric substances such as poly-α-olefins, polyethylene, polypropylene, crosslinked polyethylene, polybutylene including copolymers of α-olefins such as ethylene/propylene copolymer; dienes such as polybutadiene, polyisoprene, and the like, including copolymers with other monomers; polyurethanes and polyamides such as polyhexamethylene adipamide and polycaprolactam; polyesters such as polyethylene terephthalates; polycarbonates; polyacetals; unsaturated polyesters; polystyrene, polyethylene oxide; and copolymers such as those of high impact polystyrene containing copolymers of butadiene and styrene and those formed by the copolymerization of acrylonitrile, butadiene and/or styrene, ABS;SAN; natural and synthetic rubbers such as ethylene/propylene/diene copolymer (EPDM) and chlorinated rubber; polyphenylene oxide and copolymers; vinyl resins formed from the polymerization of vinyl halides or from the co-polymerization of vinyl halides with unsaturated polymerizable of vinyl halides with unsaturated polymerizable compounds, e.g., vinyl esters, α,β-unsaturated ketones, α,β-unsaturated aldehydes and unsaturated hydrocarbons such as butadienes and styrene; and plasticized polyvinyl chloride.

Other materials which can be stabilized by the compounds of the present invention include lubricating oil of the aliphatic ester type, i.e., di(2-ethylene) azelate and other synthetic ester lubricants, pentaerythritol tetracaproate, and the like; spinning lubricants of the polyester type; animal and vegetable derived oils, e.g., linseed oil, fat, tallow, lard, peanut oil, cod liver oil, castor oil, palm oil, corn oil, cottonseed oil, and the like; hydrocarbon materials such as gasoline, mineral oil, fuel oil, drying oil, mineral lube oils, cutting fluids, waxes, resins and the like, salts of fatty acids such as soaps and the like; and alkylene glycols, e.g., β-methoxyethylene glycol, methoxytriethylene glycol, triethylene glycol, octaethylene glycol, dibutylene glycol, dipropylene glycol and the like.

The substrates of particular importance are olefin polymers such as polyethylene, polypropylene, polybutylene and ethylene/vinyl acetate. Polypropylene is especially well stabilized with the compounds of this invention.

In general, the stabilizers of this invention are employed from about 0.01 to about 5% by weight of the stabilized composition, although this will vary with the particular substrate and application. An advantageous range is from about 0.05 to about 2% and especially from about 0.1 to about 1%.

For addition to polymeric substrates, the stabilizers can be blended before polymerization or after polymerization, during the usual processing operations, for example, by dry blending, extruder compounding and hot-milling. The composition then can be extruded, pressed, injected molded or otherwise fabricated into films, fibers, filaments, molded items and the like. The heat stabilizing properties of these compounds advantageously stabilize the polymer against degradation during such processing at the high temperature generally encountered. However, the useful life of polymeric materials is also extended by these stabilizers far beyond their ability to survive processing.

The stabilizers can also be dissolved in suitable solvents and sprayed on the surface of films, fabrics, filaments or the like to provide effective stabilization.

These compounds can also be used in combination with other additives such as sulfur-containing esters, e.g., distearyl β-thiodipropionate (DSTDP) in an amount of from 0.01 to 2% by weight of the organic material, and the like, pourpoint depressants, corrosion and rust inhibitors, dispersing agents, emulsifiers, antifoaming agents, carbon black, accelerators and other chemicals used in rubber compounding, plasticizers, color stabilizers, antistatic agents, antislip agents, antiblock agents, surface active agents, fillers, organophosphites, organothiophosphites, heat stabilizers, ultraviolet light stabiilizers, antiozonants, dyes, pigments, metal deactivators, metal chelating agents, dyesites and the like. Often combinations such as these, particularly the sulfur containing esters, the phosphites and/or the ultraviolet light stabilizers will produce superior results in certain applications to those expected by the properties of the individual components.

The following formula represents co-stabilizers which are in certain instances very useful in combination with the stabilizers of this invention:

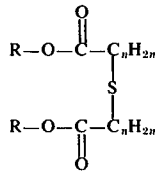

wherein R is an alkyl group having from 6 to 24 carbon atoms; and n is an integer from 1 to 6. Especially useful compounds of this type are dilauryl β-thiodipropionate and distearyl β-thiodipropionate. The above co-stabilizers are used in the amount of from 0.01 to 2% by weight of the organic material, and preferably from 0.1 to 1%.

In addition to the above noted additives that can be employed in combination with the compounds of this invention, it is often especially advantageous to employ also light stabilizers. The light stabilizers are used in the amount of from 0.01 to 5% by weight of the organic material, and preferably from 0.1 to 1%. Illustrative examples of light stabilizers are listed below.

UV-Absorbers and light protection agents 2-(2'-hydroxyphenyl)-2H-benztriazoles, such as, for example, the 5'-methyl-, 3',5'-di-tert.-butyl-, 5'-tert.-butyl-, 5'-(1,1,3,3-tetramethylbutyl)-, 5-chloro -3', 5'-di-tert.-butyl-, 5-chloro-3'-tert.-butyl 5'-methyl-, 3'-sec.-butyl-5'tert.-butyl-, 3'-{α-methylbenzyl-5'methyl-, 3'- α-methylbenzyl -5'-methyl-5-chloro-, 4'-hydroxy-, 4'-methoxy-, 4'-octoxy-, 3',5'-di-tert.-amyl-, 3'methyl-5'carbomethoxyethyl-5-chloro-3',5'-di-tert.-amyl-or 4'-tert-octyl- derivatives.

2,4-bis-(2'-hydroxyphenyl)-6-alkyl-s-triazines, such as, for example, the 6-ethyl-, 6-undecyl- or 6-heptadecyl- derivatives.

2-hydroxybenzophenones, such as, for example, the 4-hydroxy-, 4-methoxy-, 4-octoxy-, 4-decyloxy, 4-dodecyloxy-, 4-benzyloxy-, 4,2',4'-trihydroxy- or 2'-hydroxy-4,4'-dimethoxy- derivatives.

1,3-bis-(2'-hydroxybenzoyl)benzenes, such as, for example, 1,3-bis-(2'-hydroxy-4'-hexyloxybenzoyl)benzene, 1,3-bis-(2'hydroxy-4'-octoxybenzoyl)benzene and 1,3-bis-(2'-hydroxy-4'-dodecyloxybenzoyl)benzene.

Esters of optionally substituted benzoic acids, such as, for example, phenyl salicylate, octylphenyl salicylate, dibenzoylresorcinol, bis-(4-tert.-butylbenzoyl)-resorcinol, benzoylresorcinol, 3,5-di-tert.-butyl-4-hydroxybenzoic acid 2,4-di-tert.-butylphenyl ester, octadecyl ester or 2-methyl-4,6-di-tert.-butylphenyl ester, and the alkyl esters of 4-(3,5-di-tert-butyl-4-hydroxybenzoyloxy)-3,5-di-tert-butylbenzoic acid.

Acrylates, such as, for example, α-cyano-β,β-diphenylacrylic acid ethyl ester or isooctyl ester, α-carbomethoxycinnamic acid methyl ester, α-cyano-β-methyl-p-methoxycinnamic acid methyl ester or butyl ester and N-(β-carbomethoxy-vinyl)-2-methylindoline.

Nickel compounds, such as, for example, nickel complexes of 2,2'-thio-bis-4-(1,1,3,3-tetramethylbutyl)-phenol, such as the 1:1 and 1:2 complex, optionally with other ligands such as n-butyl-, triethanol-, cyclohexyl- or N-cyclohexyldiethanolamine; nickel complexes of bis- 2-hydroxy-4-(1,1,3,3-tetramethylbutyl)-phenyl sulfone, such as the 2:1 complex, optionally with other ligands such as 2-ethylcaproic acid; nickel dibutyldithiocarbamate, nickel salts of 4-hydroxy-3,5-di-tert.-butylbenzylphosphonic acid monoalkyl esters, such as the methyl, ethyl or butyl ester, the nickel complex of (2-hydroxy-4-methylphenyl)undecylketonoxime and nickel 3,5-di-tert.-butyl-4-hydroxybenzoate.

Oxalic acid diamides, such as, for example, 4,4'-dioctyloxyoxanilide, 2,2'-dioctyloxy-5,5'-di-tert.-butyloxanilide, 2,2'-didodecyloxy-5,5'-di-tert-butyloxanilide, 2-ethoxy-5-tert-butyl-2'-ethyloxanilide, 2-ethoxy-2'-ethyloxanilide, N,N'-bis-(3-dimethylaminopropyl)oxalamide, mixtures of o- and p-methoxy and o- and p-ethoxy-di-substituted oxanilides and mixtures of 2-ethoxy-5-tert.-butyl-2'-exthyloxanilide with 2-ethoxy-2'-ethyl-5,4'-di-tert.-butyloxanilide.

Sterically hindered amines, such as, for example 4-benzoyloxy-2,2,6,6-tetramethylpiperidine, 4-stearoyloxy 2,2,6,6-tetramethylpiperidine, bis-(2,2,6,6- tetramethylpiperidyl) sebacate and 3-n-octyl-7,7,9,9-tetramethyl-1,3,8-triazaspiro[4,5] decan-2,4-dione.

For exemplification purposes only listed below are compounds of this invention which are useful as stabilizers as discussed above.

2,2-bis[4-(3-methylthio-2-(3,5-di-tert-octyl-4-hydroxyhydrocinnamoyloxy))propoxyphenyl]propane 2,2-bis[4-(3-n-dodecyloxy-2-(3,5-di-tert-butyl-4-hydroxyphenylacetoxy))propoxyphenyl]butane 2,2-bis[4-(3-cyclohexylthio-2-(4-(3-methyl-5-tertbutyl-4-hydroxyphenyl)butyroxy))propoxyphenyl]butane 1,3-bis[3-(2-n-octadecylthio)ethyl-2-(3,5-di-tertamyl-4-hydroxyhydrocinnamoyloxy)-propyl]-5,5-dimethylhydantoin 2,2-bis[4-(3-n-octyloxy-2-(2,3-dimethyl-5-tert-butyl-4-hydroxyphenylacetoxy))propoxyphenyl]propane 1,3-bis[3-n-dodecylthio-2-(2-methyl-5-tert-butyl-4-hydroxyhydrocinnamoyloxy)propyl]-5,5-dimethylhydantoin The following examples are illustrative of the invention, but are not meant to limit the scope of the same in any fashion. The temperatures are given in degrees centigrade unless otherwise noted.

EXAMPLE 1

2,2-Bis-[4-(3-n-dodecylthio-2-(3-methyl-5-tert-butyl-4-hydroxyhydrocinnamoyloxy))-propoxyphenyl]propane a. A mixture of 37.3 grams (0.05 mole) of 2,2-bis-[4-(3-n-dodecylthio-2-hydroxy)propoxyphenyl]propane and 0.08 grams (0.01 mole) of lithium hydride was placed under a nitrogen atmosphere and heated to about 90°C with stirring. To this mixture was added 27.5 grams (0.11 mole) of methyl 3-methyl-5-tert-butyl-4-hydroxyhydrocinnamate. The resulting reaction mixture was stirred and heated at 125°–160°C for 3.5 hours at atmospheric pressure and then for an additional 5 hours at 140°–160°C at 1±0.3 mm pressure. The mixture was then cooled and acidified with 1.2 grams (0.02 mole) of glacial acetic acid. The crude product was dissolved in 100 ml of a 50:50 benzene: heptane mixture, treated with 3 grams of Hi-Flo Filtercel and clarified by filtration. The filtrate was percolated through a bed of 1070 grams of alumina (Woelm neutral, activity II). Elution was started with 50:50 benzene: heptane and concluded with 50:50 benzene: chloroform. The pure product fractions were combined, stripped of solvent and dried to constant weight at 80°C and 0.1 mm. The above-named ester was obtained as a viscous syrup. (Compound 1)

Calcd for $C_{73}H_{112}O_8S_2$: C,74.19; H,9.55; S,5.42. Found: C,74.15; H,9.43; S,5.06.

b. 2,2-bis[4-(3-n-dodecylthio-2-hydroxy)-propoxyphenyl]propane

To a solution of 13.7 grams (0.21 mole) of potassium hydroxide in 50 ml water was added 40.5 grams (0.20 mole) of n-dodecyl mercaptan and the mixture stirred for 15 minutes. To this new solution was added a solution of 34.0 grams (0.10 mole) of 2,2-bis[4-(2,3-epoxy)propoxyphenyl]-propane in 75 ml of warm ethanol. The resulting mixture was stirred for 16 hours at 50°C. The reaction mixture was then cooled and neutralized with 17.5 ml (0.21 mole) of concentrated hydrochloric acid yielding an oily product. 200 ml of water was added and the product extracted into ether using one 200 ml and two 100 ml portions. The combined ether extracts were washed with saturated sodium chloride solution and dried over molecule sieves (Linde 4A). After filtration and removal of the ether under vacuum, the desired product was isolated in quantitative yield (67.7 grams).

Calcd for $C_{45}H_{76}O_4S$: C,72.52; H,10.27; S,8.60. Found: C,72.67; H,10.00; S,8.48.

EXAMPLE 2

2,2-Bis-[4-(3-n-dodecylthio-2-(3,5-di-tert-butyl-4-hydroxyhydrocinnamoyloxy))propoxyphenyl]propane When in Example 1, an equivalent amount of methyl 3,5-di-tert-butyl-4-hydroxyhydrocinnamate is substituted for methyl 3-methyl-5-tert-butyl-4-hydroxyhydrocinnamate, the above-named ester is obtained as a viscous syrup.

EXAMPLE 3

2,2-Bis-[4-(3-n-octadecylthio-2-(3-methyl-5-tert-butyl-4-hydroxyhydrocinnamoyloxy))-propoxyphenyl]propane When in Example 1, an equivalent amount of 2,2-bis-[4-(3-n-octadecylthio-2-hydroxy)-propoxyphenyl]propane is substituted for 2,2-bis-[4-(3-n-dodecylthio-2-hydroxy)-propoxyphenyl]propane, the above-named ester is obtained as a viscous syrup.

EXAMPLE 4

2,2-Bis-[4-(3-methoxy-2-(3-methyl-5-tert-butyl-4-hydroxyhydrocinnamoyloxy))propoxyphenyl]propane When in Example 1, an equivalent amount of 2,2-bis-[4-(3-methoxy-2-hydroxy)propoxyphenyl]propane is substituted for 2,2-bis-[4-(3-n-dodecylthio-2-hydroxy)propoxyphenyl]propane, the above-named ester is obtained as a viscous syrup.

EXAMPLE 5

2,2-Bis-[4-(3-n-dodecylthio-2-(2,3-dimethyl-5-tert-butyl-4-hydroxyhydrocinnamoyloxy))-propoxyphenyl]propane When in Example 1, an equivalent amount of methyl 2,3-dimethyl-5-tert-butyl-4-hydroxyhydrocinnamate is substituted for methyl 3-methyl-5-tert-butyl-4-hydroxyhydrocinnamate, the above-named ester is obtained as a viscous liquid.

EXAMPLE 6

1,3-Bis[3-n-dodecylthio-2-(3-methyl-5-tert-butyl-4-hydroxyhydrocinnamoyloxy)propyl]-5,5-dimethylhydantoin When in Example 1, an equivalent amount of 1,3-bis(3-n-dodecylthio-2-hydroxypropyl)-5,5-dimethylhydantoin is substituted for 2,2-bis[4-(3-n-dodecylthio-2-hydroxy)-propoxyphenyl]propane, the above named ester is obtained.

EXAMPLE 7

1,3-Bis[3-n-octadecylthio-2-(3,5-di-tert-butyl-4-hydroxyhydrocinnamoyloxy)propyl]-5-ethyl-5-methylhydantoin When in Example 2, an equivalent amount of 1,3-bis(3-n-octadecylthio-2-hydroxypropyl)-5-ethyl-5-methylhydantoin is substituted for 2,2-bis[4-(3-n-dodecylthio-2-hydroxy)propoxyphenyl]propane, the above-named ester is obtained.

EXAMPLE 8

Unstabilized polypropylene powder (Hercules Profax 6501) was thoroughly blended with 0.2% by weight of the indicated stabilizer compound. Also prepared were samples of polypropylene containing 0.1% by weight of the same stabilizer and 0.3% by weight of distearyl β-thiodipropionate (DSTDP). The blended materials were then milled on a two-roll mill at 182°C for 10 minutes after which time the stabilized polypropylene was sheeted from the mill and allowed to cool.

The milled polypropylene sheets were then cut into pieces and pressed for 7 minutes on a hydraulic press at 218°C and 275 psi (19.25 Kg/cm$^2$) pressure. The resulting plaques of 25 mil (0.635 mm) thickness were tested for resistance to accelerated aging in a forced draft oven at 150°C. When the plaques showed the first signs of decomposition (e.g. cracking or brown edges) they were considered to have failed. The results are shown in Table I below.

Table I

| Oven Aging of Polypropylene Plaques | |
|---|---|
| Percent Stabilizer | Hours to Failure |
| Unstabilized Polypropylene | 3 |
| 0.3% DSTDT only | 100 |
| 0.2% Compound 1 | 690 |
| 0.1% Compound 1 + 0.3% DSTDP | 1420 |
| 0.5% 2-(n-octadecylthio)ethyl 3.5-di-tert-butyl-4-hydroxy-phenylacetate (Example 1, US 3,285,855) | 1000 |
| 0.5% 2-(n-octadecylthio)ethyl 3-(3,5-di-tert-butyl-4-hydroxyphenyl)-propionate (Example 2, US 3,285,855) | 1220 |
| 0.5% 2-(n-octadecylthio)ethyl 3,5-di tert-butyl-4-hydroxybenzoate (Example 3, US 3,285,855) | 740 |
| 0.5% β-thiodiethylene bis-(3,5-di-tert-butyl-4-hydroxyphenylacetate) | 460 |
| 0.5% β-thiodiethylene bis-[3-(3,5-di-tert-butyl-4-hydroxyphenyl)-propionate] | 1350 |
| 0.5% oxydiethylene bis-[3-(3,5-di-tert-butyl-4-hydroxyphenyl)propionate] | 1000 |
| 0.5% n-octadecyl 3-(3,5-di-tert-butyl-4-hydroxyphenyl)propionate (Example 4, US 3,285,855) | 630 |
| 0.5% pentaerythritol tetrakis[3-(3,5-di-tert-butyl-4-hydroxyphenyl)-propionate] (Example 6, US 3,285,855) | 1470 |
| 0.3% same stabilizer (Example 5, US 3,758,549) | 1170 |
| 0.1% same stabilizer + 0.5% dilauryl β-thiodipropionate (Example 6, US 3,285,855) | 975 |
| 0.5% 1,2-propylene bis[3-(3,5-di-tert-butyl-4-hydroxyphenyl)propionate] (Example 7, US 3,285,855) | 780 |
| 0.5% ethylene bis(3,5-di-tert-butyl-4-hydroxyphenylacetate) | 475 |
| 0.5% ethylene bis[3-(3,5-di-tert-butyl-4-hydroxyphenyl)propionate] | 820 |
| 0.5% 2,2-dimethylpropylene bis[3-(3,5-di-tert-butyl-4-hydroxyphenyl)-propionate] | 510 |
| 0.5% 1,1,1-butanetriyl tris[3-(3,5-di-tert-butyl-4-hydroxyphenyl)-propionate] | 1750 |
| 0.2% 2,4,4-trimethylhexylene (70%) + 2,2,4-trimethylhexylene (30%) bis[3-(3,5-di-tert-butyl-4-hydroxyphenyl)propionate] (Example 5, US 3,779,945) [40 mil(1 mm) thick films tested] | 936 |
| 0.1% above mixed ester stabilizer + 0.3% dilauryl β-thiodipropionate [40 mil (1 mm) thick films tested] | 1080 |

The esters of this invention are particularly active in the presence of a thio ester co-stabilizer.

The esters of this invention of 0.2% concentration are in some cases more effective than the 2-(n-octadecylthio)-ethyl esters described in U.S. Pat. Nos. 3,285,855 and 3,441,575 tested at the 0.5% concentration in polypropylene. Thus the esters of this invention at 40% of the concentration of the most closely related prior art stabilizers exhibit comparable performance as seen in Example 8.

In comparison with the liquid mixed esters (Example 5, U.S. Pat. No. 3,779,945) thinner films (25 mil vs 40 mil) were used with the esters of this invention which still exhibited far superior performance in the presence of a thio ester co-stabilizer in the thinner films than did the liquid mixed esters in a comparable formulation tested in thicker films which would normally be expected to be more stable.

EXAMPLE 9

Test specimens were prepared exactly as described in Example 8 except that the stabilized polypropylene contained 0.2% by weight of the various esters of this invention and 0.5% by weight of 2-(2-hydroxy-3,5-di-tert-butylphenyl)-5-chloro-2H-benzotriazole as a co-stabilizer. Results of accelerated aging tests in a forced draft oven at 150°C are shown in Table II below Table II

| Compound Number (plus co-stabilizer) | Oven Aging at 150°C Hours to Failure |
|---|---|
| Unstabilized Polypropylene | 3 |
| 1 | 680 |

EXAMPLE 10

Pellets (500 g) of unstabilized nylon-6,6 (Zytel 101, DuPont) are placed in a Kitchen Aid Mixer. With mixing a solution of 0.5% (based on the weight of nylon) of 2,2-bis[4-(3-n-octadecylthio-2-(2,3-diethyl-5-tert-butyl-4-hydroxyhydrocinnamoyloxy))-propoxyphenyl]-propane in 20 ml of methylene chloride is added slowly. Sodium hypophosphite (0.5 gm 0.14) is dissolved in 20 ml of water and added slowly with mixing to the nylon pellets after the antioxidant solution has been added and most of the methylene chloride has evaporated. The stabilized pellets are dried at 80°C at <<1 mm Hg. for 4 hours.

The polyamide formulation is extruded at 600°F (315.6°C) through at one-fourth inch (0.635 cm) die into a rod which is water cooled and chopped into pellets. A three-fourth inch (1.905 cm) Brabender extruder, equipped with a nylon screw, is used. The pellets are dried at 80°C at <1 mm for 4 hours.

The dried pellets are compression molded into 5 mil (0.127 mm) thick film by pressing at 290°C for 4 minutes at 6000 psi (57.75 Kg/cm$^2$). The films are oven aged at 150°C in a forced draft oven and samples are removed periodically. The specific viscosity of the samples are determined using a 1% formic acid solution at 25°C. The sample stabilized with the above noted stabilizer required longer aging time to reduce its viscosity by one-half than the unstabilized sample.

EXAMPLE 11

Unstabilized high impact polystyrene resin is dry blended with 0.01% by weight of the resin of 2,2-bis[4-(3-n-hexadecylthio-2-(2,3-dimethyl-5-tert-butyl-4-hydroxyphenylacetoxy))propoxyphenyl]propane. The resin is then extrusion compounded on a 1 inch (2.54 cm) 24/1=L/D extruder, melt temperature 500°F (260°C) and pressed for 7 minutes at a temperature of 163°C and a pressure of 2000 psi (140 Kg/cm²) into a sheet of uniform thickness of 100 mil (2.54 mm). The sheets are then cut into plaques of 2 inch × 2 inch (5.08 cm × 5.08 cm.). The plaques are then oven aged at 80°C and color measurements made periodically using a Hunter Color Difference Meter Model D25. The polystyrene samples stabilized with the above stabilizer develops the undesirable yellow disoloration substantially later than the time that such discoloration occurred in the unstabilized samples.

EXAMPLE 12

Unstabilized linear polyethylene (HiFax 4401) is solvent blended in methylene chloride with 0.2 by weight of the substrate of 1,3 -bis[3-n-dodecylthio-2-(3-methyl-5-tert-octyl-4-hydroxyhydrocinnamoyloxy)-propyl]-5,5-dimethylhydantoin and then vacuum dried. The resin is then extruded at 450°F (232.2°C) using a three-fourth inch (1.905 cm) extruder having a 24:1 L/D ratio. The melt flow rate of a sample of the resin is determined after each extrusion according to ASTM test D-1238. Polyethylene stabilized with above compound is found to undergo less change in the melt flow rate than the unstabilized polyethylene.

EXAMPLE 13

A quantity of SBR emulsion containing 100 g of rubber (500 ml of a 20% SBR emulsion obtained commercially from Texas U.S. as Synpol 1500) previously stored under nitrogen, is placed in a beaker and stirred vigorously. The pH of the emulsion is adjusted to 10.5 with a 0.5N NaOH solution.

To the emulsion is added 50 ml of 25% NaCl solution. A 6% NaCl solution adjusted with hydrochloric acid to a pH 1.5 is added in a thin stream with vigorous stirring. When pH 6.5 is reached, the rubber begins to coagulate and the addition is slowed down in order to maintain uniform agitation. The addition of the acidic 6% NaCl solution is terminated when a pH 3.5 is reached. The coagulated crumb-rubber slurry at pH 3.5 is stirred for one-half hour.

The coagulated rubber is isolated by filtration through cheese cloth, and rinsed with distilled water. After three subsequent washings with fresh distilled water, the coagulated rubber is dried, first at 25 mm Hg and finally to constant weight under high vacuum (<1 mm) at 40° to 45°C.

The dried rubber (25 g) is heated under nitrogen at 125°C in a Brabender mixer and to this is added with mixing 0.1% by weight of 2,2-bis[4-(3-cyclohexylthio-2-(3-methyl-5-tert-amyl-4-hydroxybenzoxy))propoxyphenyl]propane.

Portions of the rubber are oven aged at 100°C. At various intervals gel content is determined on the rubber. The rubber stabilized with the above compound shows much less gel formation than the unstabilized sample.

EXAMPLE 14

To 50 g of polyacetal resin containing 0.1% of an acid scavenger, dicyandiamide, is added 0.2% by weight of 2,2-bis[4-(3-methylthio-2-(3,5-di-tert-octyl-4-hydroxyphenylacetoxy))propoxyphenyl]propane, and milled for 7 minutes at 200°C in a Brabender Plastirecorder. The milled formulation is subsequently pressed into a 40 mil (1.016 mm) sheet at 215°C at 350 psi (24.5 Kg/cm²) for 90 seconds then cooled quickly in a cold press at 350 psi (24.5 Kg/cm²). The stabilized sheets are then remolded for 2 minutes at contact pressure and for 3 minutes at 300 psi (21 Kg/cm²) at 215°C to give plaques 1.5 inches × 1.5 inches × 125 mil (3.81 cm × 5.715 cm × 3.175 mm.). The plaques are aged in the oven at 60°C and the weight loss of the specimen is determined periodically until a 4% weight loss is reached. The stabilized sample takes a much longer time to reach this 4% weight loss than does the unstabilized sample.

EXAMPLE 15

Unstabilized, thoroughly dried polyethylene terephthalate chips are dry blended with 1.0% by weight of 2,2-bis[4-(3-n-octylthio-2-(6-(3,5-di-tert-butyl-4-hydroxyphenyl)caproyloxy))propoxyphenyl]propane. 60/10 denier multifilament is melt spun at a melt temperature of 290°C and cold oriented 3 to 1. The oriented fibers are wound into skeins and oven aged at 140°C. The stabilized material exhibits greater retention of tensile strength after 24 hours than the unstabilized material.

EXAMPLE 16

A stabilized high temperature lubricating oil is prepared by incorporating 0.05% by weight of 2,2-bis[4-(3-n-octadecylthio-2-(5-(3,5-di-tert-butyl-4-hydroxyphenyl)valeroyloxy))propoxyphenyl]propane to the lubricant which comprises diisoamyl adipate. The stabilized composition is compared with the unstabilized lubricant by heating at 175°C in the presence of air and metallic catalysts according to the test method described in Military Specification Mil-I-7808c. After 72 hours, the blank containing no stabilizer contains more sludge and has a greater viscosity than the stabilized lubricant.

What is claimed is:

1. A compound having the formula

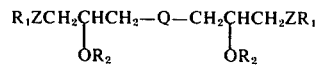

wherein $R_1$ is alkyl of 1 to 30 carbon atoms, cycloalkyl of 5 to 12 carbon atoms, alkylthioethyl of 4 to 27 atoms in the chain or alkylpolyoxyalkylene of 4 to 27 atoms in the chain having the general structure $R°(OC_nH_{2n})_h$ or $R°(OCH_2CHR')_h$ where $R°$ is alkyl of 1 to 18 carbon atoms, $n$ is 2 to 4, $R'$ is hydrogen, methyl or ethyl and $h$ is 1 to 3, $R_2$ is the group

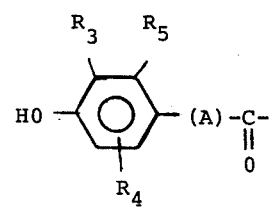

$R_3$ is hydrogen, alkyl of 1 to 8 carbon atoms, cycloalkyl of 5 to 6 carbon atoms or α-methylbenzyl, $R_4$ is alkyl of 1 to 8 carbon atoms or cycloalkyl of 5 to 6 carbon atoms, $R_5$ is hydrogen or lower alkyl of 1 to 4 carbon atoms or $R_3$ and $R_5$ together are a butylene chain which, together with the phenyl ring, form a tetrahydronaphthyl group, and provided when $R_3$ is hydrogen, $R_5$ is alkyl and $R_4$ is located on the carbon atom ortho to the hydroxyl group, A is a covalent carbon bond or a straight or branched lower alkylene having 1 to 8 carbon atoms, Q is the group

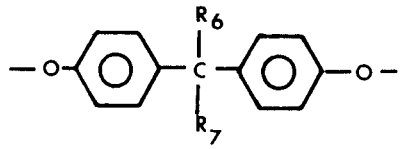

$R_6$ is hydrogen or alkyl of 1 to 4 carbon atoms, $R_7$ is hydrogen or alkyl of 1 to 8 carbon atoms, and Z is oxygen or sulfur.

2. A compound according to claim 1 wherein
$R_1$ is alkyl of 1 to 18 carbon atoms,
$R_3$ is hydrogen or alkyl of 1 to 4 carbon atoms,
$R_4$ is branched alkyl of 3 to 8 carbon atoms,
$R_5$ is hydrogen or alkyl of 1 to 3 carbon atoms,
A is a straight chain alkylene of 1 to 3 carbon atoms,
$R_6$ is hydrogen or methyl, and
$R_7$ is hydrogen or alkyl of 1 to 3 carbon atoms.

3. A compound according to claim 1 wherein
$R_1$ is alkyl of 8 to 18 carbon atoms,
$R_3$ is methyl or tert-butyl,
$R_4$ is tert-butyl,
$R_5$ is hydrogen or methyl,
A is methylene or ethylene,
$R_6$ is methyl, and
$R_7$ is methyl.

4. The compound according to claim 1 which is 2,2-bis[4-(3-n-dodecylthio-2-(3-methyl-5-tert-butyl-4-hydroxyhydrocinnamoyloxy))propoxyphenyl]propane.

* * * * *